(12) United States Patent
Miyaura et al.

(10) Patent No.: US 8,143,407 B2
(45) Date of Patent: Mar. 27, 2012

(54) PROCESS FOR PRODUCTION OF HETEROARYL-TYPE BORON COMPOUNDS WITH IRIDIUM CATALYST

(75) Inventors: Norio Miyaura, Sapporo (JP); Tatsuo Ishiyama, Sapporo (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 203 days.

(21) Appl. No.: 12/560,707

(22) Filed: Sep. 16, 2009

(65) Prior Publication Data

US 2010/0010224 A1 Jan. 14, 2010

Related U.S. Application Data

(62) Division of application No. 10/505,460, filed on Sep. 2, 2004, now Pat. No. 7,612,218.

(30) Foreign Application Priority Data

Mar. 6, 2002 (JP) ................................ 2002-061044

(51) Int. Cl.
*C07D 421/00* (2006.01)
(52) U.S. Cl. .................................................. 546/268.1
(58) Field of Classification Search ............... 546/268.1
See application file for complete search history.

(56) References Cited

U.S. PATENT DOCUMENTS 6,878,830 B2 * 4/2005 Smith, III ..................... 548/402

FOREIGN PATENT DOCUMENTS

| WO | 98/45265 | 10/1998 |
| WO | WO 03/006158 A2 | 1/2003 |
| WO | WO 03/006403 A2 | 1/2003 |

OTHER PUBLICATIONS

Jun Takagi, et al., "Iridium-catalyzed C-H couping reaction of heteroaromatic compounds with bis(pinacolato)diboron: regioselective synthesis of heteroarylboronates", Tetrahedron Letters, vol. 43, No. 32, pp. 5649-5651 2002.
Jian-Yang Cho, et al., "Remarkably Selective Iridium Catalysts for the Elaboration of Aromatic C-H Bonds", WWW.SC ENCEMAG. ORG, Science, XP002462049, vol. 295, Jan. 11, 2002, pp. 305-308.
Tatsuo Ishiyama, et al., "A Stoichiometric Aromatic C-H Borylation Catalyzed by Iridium ($_I$) /2,2'-Bipyridine Complexes at Room Temperature", Angewandte Chemie International Edition, XP002462051, vol. 41, No. 16, 2002, pp. 3056-3058.
Takagi et al., Tetrahedron Letters, 2002, 43:5649-5651.
Tagata et al., Advanced Synthesis & Catalysis, 2004, 346(13-15):1655-1660.
Melaimi, Mohand et al. "Bis(diphosphaferrocene) palladium(II) dimer complexes as efficient catalysts in the synthesis of arylboronic esters" Journal of Organometallic Chemistry, 2001, 640(1-2), 197-199.
Ishiyama, Tatsuo et al. "Synthesis of pinacol arylboronates via cross-coupling reaction of bis(pinacolato)diboron with chloroarenes catalyzed by palladium(0)-tricyclohexylphosphine complexes" Tetrahedron, 2001, 57 (49), 9813-9816.
Tse, Man Kin et al. Regioselective Aromatic Borylation in an Inert Solvent, Organic Letters, 2001, 3 (18), 2831-2833.
Jayakannan, M. et al. Mechanistic Aspects of the Suzuki Polycondensation of Thiophenebisboronic Derivatives and Diiodobenzenes Analyzed by MALDI-TOF Mass Spectrometry, Macromolecules, 2001, 34 (16), 5386-5393.

* cited by examiner

*Primary Examiner* — Rei-tsang Shiao
(74) *Attorney, Agent, or Firm* — Oblon, Spivak, McClelland, Maier & Neustadt, L.L.P.

(57) ABSTRACT

The present invention provides an economically and industrially superior simple process that enables the selective production of an aromatic heterocyclic monoboron compound and aromatic heterocyclic diboron compound at a satisfactory yield and in a desired ratio by reacting an aromatic heterocyclic compound and a boron compound in a single step under mild conditions while changing only the charged ratios of the raw materials.

The present invention provides a production process of a heteroaryl mono- or diboron compound comprising an aromatic heterocyclic compound and a boron compound in the form of bis(pinacolate)diboron or pinacolate diborane in the presence of a iridium-containing catalyst and a ligand such as a bipyridyl ligand.

15 Claims, No Drawings

PROCESS FOR PRODUCTION OF HETEROARYL-TYPE BORON COMPOUNDS WITH IRIDIUM CATALYST

TECHNICAL FIELD

The present invention relates to a production process of an aromatic heterocyclic boron compound that uses an iridium-containing catalyst. An aromatic heterocyclic boron compound produced according to the present invention can be used as a reaction substrate when producing biaryl derivatives and polyaryl derivatives that are useful as pharmaceutical and agricultural chemical intermediates as well as functional organic materials.

BACKGROUND ART

Various processes have been proposed in the prior art for boronation of aromatic hydrocarbons. For example, processes are known for lithionation, halogenation or boronation after converting to a trifurate of a benzene ring, examples of which include (1) a process using aryl halide or aryl trifurate and pinacol diboron (P. Rocca et al., J. Org. Chem., 58, 7832, 1993), (2) a process involving reaction with boric ester following lithionation of an aromatic ring, and (3) a process involving reaction with boric ester following reaction of aryl halide with magnesium (A. R. Martin, Y. Yang, Acta. Chem. Scand., 47, 221, 1993).

In addition, known examples of direct boronation of benzene include (4) a process that uses a boron halide (T. R. Kelly et al., Tetrahedron Lett., 35, 7621 (1994), P. D. Hobbs et al., J. Chem. Soc. Chem. Commun., 923 (1996), T. R. Hoye, M. Chen, J. Org. Chem., 61, 7940 (1996)), (5) a process that uses an Ir-based catalyst (Iverson, C. N., Smith, M. R., III. J. Am. Chem. Soc., 121, 7696 (1999)), (6) a process that uses an Re-based catalyst (Chen. H., Hartwig, J. F., Agnew. Chem. Int. Ed., 38, 3391 (1999)), (7) a process that uses an Rh-based catalyst (Chen, H., Hartwig, J. F., Science, 287, 1995 (2000), Cho, J. Y., Iverson, C. N., Smith, M. R., III. J. Am. Chem. Soc., 122, 12868 (2000), Tse, M. K., Cho, J. Y., Smith, M. R., III. Org. Lett., 3, 2831 (2001), Shimada, S., Batsanov, A. S., Howard, J. A. K, Marder, T. B., Angew. Chem. Int. Ed., 40, 2168 (2001)), and (8) a process that uses an Ir-based catalyst (Cho, J. Y., Tse, M. K., Holmes, Science, 295, 305 (2002), Ishiyama, T., Takagi, J., Ishida, K., Miyaura, N., Anastasi, N. R., Hartwig, J. F., J. Am. Chem. Soc., 124, 390 (2002)).

However, there are few examples of boronation reactions of aromatic heterocyclic compounds, with the only known example being (9) a process in which silver acetate is allowed to act on indole followed by reaction with borane followed additionally by hydrolysis (K. Kamiyama, T. Watanabe, M. Uemura, J. Org. Chem., 61, 1375 (1996)).

Although the processes (1) through (9) are known as examples of boronation of an aromatic ring as mentioned above, these examples of the prior art have the following disadvantages. The processes of (1) through (3) have a large number of steps for carrying out lithionation, halogenation or trifluorination of a benzene ring, thereby resulting in problems with industrial production. Moreover, process (1) only uses one of the two borons of the diboron used, thereby making it uneconomical, while processes (2) and (3) are subjected to considerable restrictions on the functional groups of the substrate used due to going through a highly reactive intermediate. Process (4) has the disadvantages of harsh reaction conditions, low yield and the formation of isomerism in the case of substrates having functional groups. In the processes of (5) through (7), the catalyst is difficult to acquire while also having the problem of requiring harsh reaction conditions. In process (8), although there are some processes that enable boronation of a benzene ring to take place with high yield and in a single step, there are no known application examples for the aromatic heterocyclic ring. In the process of (9) involving application of boronation to a complex ring, there is the disadvantage of having to react borane, which is associated with the risk of toxicity and explosiveness, after allowing harmful silver acetate to act on indole. In consideration of these circumstances, there is a need for the development of a novel boronation reaction for aromatic complex rings that is able to overcome the aforementioned problems.

DISCLOSURE OF THE INVENTION

As a result of conducting extensive studies to resolve the aforementioned problems, the inventors of the present invention developed a novel boronation of an aromatic heterocyclic compound, and established a production process of extremely useful aromatic heterocyclic boron compounds that uses an easily prepared iridium catalyst and bipyridine derivative as ligands, allows the reaction to proceed efficiently under mild conditions, produces few byproducts, and enables mono- and/or diboronation of an aromatic heterocyclic compound in a single step, thereby leading to completion of the present invention.

Namely, a first aspect of the present invention relates to a production process of a heteroaryl boron compound represented with general formula (V) or (VI):

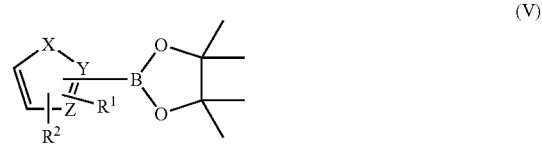

(V)

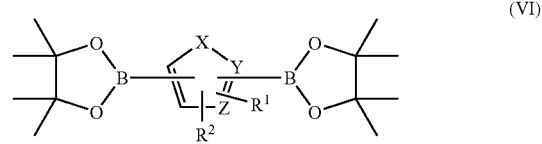

(VI)

(wherein, X, Y, Z, $R^1$ and $R^2$ are the same as defined below) comprising: reacting an aromatic heterocyclic compound represented with the following general formula (I):

(I)

(wherein, X represents an oxygen atom, sulfur atom or an imino group which may have a substituent, Y and Z may be the same or different and respectively represent —CH= or —N=, $R^1$ and $R^2$ may be the same or different and respectively represent a hydrogen atom, linear or branched $C_{1-8}$ alkyl group, linear or branched $C_{1-8}$ alkoxy group, nitro group, cyano group, halogenated $C_{1-8}$ alkyl group, halogen atom, carbamoyl group, $C_{1-8}$ acyl group, $C_{1-8}$ alkoxycarbonyl group, amino group which may have a substituent, or the following general formula (II) in which $R^1$ and $R^2$ are adjacent and form a ring:

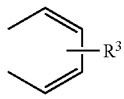

(II)

(wherein, $R^3$ represents a hydrogen atom, a linear or branched $C_{1-8}$ alkyl group, a linear or branched $C_{1-8}$ alkoxy group, nitro group, cyano group, halogenated $C_{1-8}$ alkyl group, halogen atom, carbamoyl group, $C_{1-8}$ acyl group, $C_{1-8}$ alkoxycarbonyl group or amino group that may have a substituent)) with a boron compound represented with the following general formula (III) or (IV):

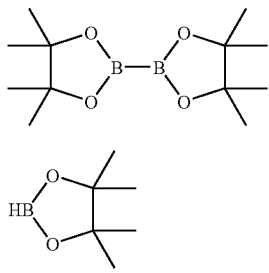

(III)

(IV)

in the presence of an iridium-containing catalyst and a ligand.

A second aspect of the present invention relates to a production process of a heteroaryl boron compound represented with general formula (VIII) or (IX):

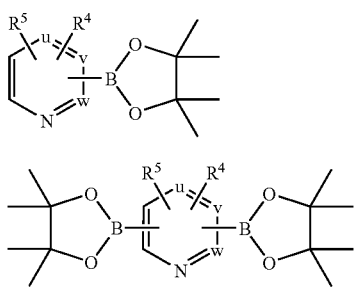

(VIII)

(IX)

(wherein, u, v, w, $R^4$ and $R^5$ are the same as defined below) comprising: reacting an aromatic heterocyclic compound represented with the following general formula (VII):

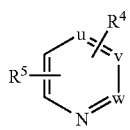

(VII)

(wherein, u, v and w may be the same or different and respectively represent —CH= or —N=, and $R^4$ and $R^5$ may be the same or different and respectively represent a hydrogen atom, linear or branched $C_{1-8}$ alkyl group, linear or branched $C_{1-8}$ alkoxy group, nitro group, cyano group, halogenated $C_{1-8}$ alkyl group, halogen atom, carbamoyl group, $C_{1-8}$ acyl group, $C_{1-8}$ alkoxycarbonyl group, amino group which may have a substituent, or the following general formula (II) in which $R^4$ and $R^5$ are adjacent and form a ring:

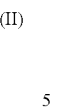

(II)

(wherein, $R^3$ represents a hydrogen atom, a linear or branched $C_{1-8}$ alkyl group, linear or branched $C_{1-8}$ alkoxy group, nitro group, cyano group, halogenated $C_{1-8}$ alkyl group, halogen atom, carbamoyl group, $C_{1-8}$ acyl group, $C_{1-8}$ alkoxycarbonyl group or amino group that may have a substituent)) with a boron compound represented with the following general formula (III) or (IV):

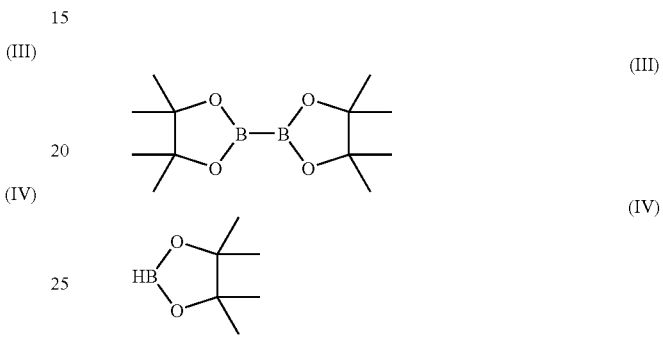

(III)

(IV)

in the presence of an iridium-containing catalyst and a ligand.

BEST MODE FOR CARRYING OUT THE INVENTION

The following provides a detailed explanation of the present invention. Any aromatic heterocyclic compound can be used for the aromatic heterocyclic compound used as a raw material in the present invention provided it has at least one aromatic $sp^2C$—H bond. Specific examples of aromatic heterocyclic compound (I) or (VII) include furan; alkyl furans such as 2-methyl furan, 3-methyl furan, 2-ethyl furan, 3-isopropyl furan, 2-isopropyl furan, 2-butyl furan, 3-butyl furan, 2-isobutyl furan, 3-isobutyl furan, 3,4-dimethyl furan, 3-butyl-4-methyl furan, 2,5-dimethyl furan, 3,4-diisopropyl furan, 2-isopropyl-3-methyl furan, 3-butyl-4-isopropyl furan and 2-butyl-5-isopropyl furan; alkoxy furans such as 3-methoxy furan, 2-ethoxy furan, 3-butoxy furan, 2-isopropoxy furan, 2-methoxy furan and 3-ethoxy furan; nitrofurans such as 3-nitrofuran and 2-nitrofuran; cyanofurans such as 3-cyanofuran and 2-cyanofuran; halofurans such as 2-chlorofuran, 3-chlorofuran, 4-chlorofuran and 2-bromofuran; halogenated alkyl furans such as 3-trifluoromethyl furan and 2-trifluoromethyl furan; carbamoyl furans such as 3-carbamoyl furan, 2-dimethylcarbamoyl furan and 4-dimethylcarbamoyl furan; acyl furans such as 3-acetyl furan, 2-acetyl furan and 3-butanoyl furan; alkoxycarbonyl furans such as 3-methoxycarbonyl furan, 2-methoxycarbonyl furan and 3-ethoxycarbonyl furan; N-substituted amino furans such as 2-amino furan, 3-amino furan, 2-dimethylamino furan and 3-dimethylamino furan; alkyl halofurans such as 4-chloro-3-butyl furan and 4-methyl-2-chlorofuran; alkoxyalkyl furans such as 2-methoxy-3-methyl furan, 2-methoxy-4-methyl furan and 2-ethoxy-5-methyl furan; cyano-substituted chlorofurans such as 3-chloro-2-cyanofuran, 3-chloro-4-cyanofuran, 3-chloro-5-cyanofuran, 4-chloro-2-cyanofuran and 4-chloro-3-cyanofuran; nitro-substituted chlorofurans such as 3-chloro-2-nitrofuran, 3-chloro-4-nitrofuran, 3-chloro-5-nitrofuran, 4-chloro-2-nitrofuran and 4-chloro-3-nitrofuran;

aminochlorofurans such as 3-chloro-4-amino furan, 3-chloro-5-dimethylamino furan, 4-chloro-2-dimethylamino furan and 4-chloro-3-dimethylamino furan; carbamoylchlorofurans such as 3-chloro-4-carbamoyl furan, 3-chloro-5-dimethylcarbamoyl furan, 4-chloro-2-dimethylcarbamoyl furan and 4-chloro-3-dimethylcarbamoyl furan; halogenated alkyl furans such as 4-chloro-2-trifluoromethyl furan and 4-chloro-3-trifluoromethyl furan; benzofuran; alkyl benzofurans such as 6-methyl benzofuran, 4-methyl benzofuran, 5-methyl benzofuran, 4-isopropyl benzofuran, 2-isopropyl benzofuran, 6-isopropyl benzofuran, 3-isobutyl benzofuran, 5,6-dimethyl benzofuran, 4-butyl-6-methyl benzofuran, 2,5-dimethyl benzofuran, 3,4-diisopropyl benzofuran, 4-isopropyl-5-methyl benzofuran, 4-butyl-6-isopropyl benzofuran and 2-butyl-5-isopropyl benzofuran; alkoxy benzofurans such as 4-methoxy benzofuran, 4-ethoxy benzofuran, 5-butoxy benzofuran, 6-isopropoxy benzofuran, 5-methoxy benzofuran, 6-ethoxy benzofuran and 2-methoxy benzofuran; nitrobenzofurans such as 4-nitrobenzofuran and 5-nitrobenzofuran; cyanobenzofurans such as 4-cyanobenzofuran and 5-cyanobenzofuran; halobenzofurans such as 4-chlorobenzofuran, 5-chlorobenzofuran, 6-chlorobenzofuran and 4-bromobenzofuran; halogenated alkyl benzofurans such as 4-trifluoromethyl benzofuran and 5-trifluoromethyl benzofuran; carbamoyl benzofurans such as 4-carbamoyl benzofuran, 5-dimethylcarbamoyl benzofuran and 6-dimethylcarbamoyl benzofuran; acyl benzofurans such as 4-acetyl benzofuran, 5-acetyl benzofuran and 6-butanoyl benzofuran; alkoxycarbonyl benzofurans such as 4-methoxycarbonyl benzofuran, 5-methoxycarbonyl benzofuran and 6-ethoxycarbonyl benzofuran; N-substituted amino benzofurans such as 4-amino benzofuran, 5-amino benzofuran, 6-dimethylamino benzofuran and 4-dimethylamino benzofuran; alkyl halobenzofurans such as 4-chloro-5-butyl benzofuran and 4-methyl-6-chlorobenzofuran; alkoxyalkyl benzofurans such as 2-methoxy-4-methyl benzofuran, 2-methoxy-5-methyl benzofuran and 2-ethoxy-5-methyl benzofuran; halocyanobenzothiophen such as 4-chloro-6-cyanobenzofuran; thiophene; alkyl thiophenes such as 3-methyl thiophene, 4-methyl thiophene, 5-methyl thiophene, 3-isopropyl thiophene, 2-isopropyl thiophene, 4-isopropyl thiophene, 5-isopropyl thiophene, 2-isopropyl thiophene, 3-isobutyl thiophene, 3,4-dimethyl thiophene, 3-butyl-4-methyl thiophene, 2,5-dimethyl thiophene, 3,4-diisopropyl thiophene, 2-isopropyl-3-methyl thiophene, 3-butyl-4-isopropyl thiophene and 2-butyl-5-isopropyl thiophene; alkoxy thiophenes such as 3-methoxy thiophene, 2-ethoxy thiophene, 3-butoxy thiophene, 2-isopropoxy thiophene, 2-methoxythiophene, 3-ethoxythiophene and 2-methoxy thiophene; nitrothiophenes such as 3-nitrothiophene and 2-nitrothiophene; cyanothiophenes such as 3-cyanothiophene and 2-cyanothiophene; halothiophenes such as 2-chlorothiophene, 3-chlorothiophene, 4-chlorothiophene and 2-bromothiophene; halogenated alkyl thiophenes such as 3-trifluoromethyl thiophene and 2-trifluoromethyl thiophene; carbamoyl thiophenes such as 3-carbamoyl thiophene, 2-dimethylcarbamoyl thiophene and 4-dimethylcarbamoyl thiophene; acyl thiophenes such as 3-acetyl thiophene, 4-acetyl thiophene and 3-butanoyl thiophene; alkoxycarbonyl thiophenes such as 3-methoxycarbonyl thiophene, 2-methoxycarbonyl thiophene and 3-ethoxycarbonyl thiophene; N-substituted amino thiophenes such as 2-amino thiophene, 3-amino thiophene, 2-dimethylamino thiophene and 3-dimethylamino thiophene; alkylhalothiophenes such as 4-chloro-3-butyl thiophene and 4-methyl-2-chlorothiophene; alkoxyalkyl thiophenes such as 2-methoxy-3-methyl thiophene, 2-methoxy-4-methyl thiophene and 2-ethoxy-5-methyl thiophene; cyanochlorothiophenes such as 3-chloro-2-cyanothiophene, 3-chloro-4-cyanothiophene, 3-chloro-5-cyanothiophene, 4-chloro-2-cyanothiophene and 4-chloro-3-cyanothiophene; nitrochlorophenes such as 3-chloro-2-nitrothiophene, 3-chloro-4-nitrothiophene, 3-chloro-5-nitrothiophene, 4-chloro-2-nitrothiophene and 4-chloro-3-nitrothiophene; aminochlorothiophenes such as 3-chloro-4-amino thiophene, 3-chloro-5-dimethyl amino thiophene, 4-chloro-2-dimethyl amino thiophene and 4-chloro-3-dimethyl amino thiophene; carbamoyl chlorothiophenes such as 3-chloro-4-carbamoyl thiophene, 3-chloro-5-dimethylcarbamoyl thiophene, 4-chloro-2-dimethylcarbamoyl thiophene and 4-chloro-3-dimethylcarbamoyl thiophene; halogenated alkyl halothiophenes such as 4-chloro-2-trifluoromethyl thiophene and 4-chloro-3-trifluoromethyl thiophene; benzothiophene; alkyl benzothiophenes such as 6-methyl benzothiophene, 4-methyl benzothiophene, 5-methyl benzothiophene, 4-isopropyl benzothiophene, 2-isopropyl benzothiophene, 6-isopropyl benzothiophene, 3-isobutyl benzothiophene, 5,6-dimethyl benzothiophene, 4-butyl-6-methyl benzothiophene, 2,5-dimethyl benzothiophene, 3,4-diisopropyl benzothiophene, 4-isopropyl-5-methyl benzothiophene, 4-butyl-6-isopropyl benzothiophene and 2-butyl-5-isopropyl benzothiophene; alkoxy benzothiophenes such as 4-methoxy benzothiophene, 4-ethoxy benzothiophene, 5-butoxy benzothiophene, 6-isopropoxy benzothiophene, 5-methoxy benzothiophene, 6-ethoxy benzothiophene and 2-methoxy benzothiophene; nitrobenzothiophenes such as 4-nitrobenzothiophene and 5-nitrobenzothiophene; cyanobenzothiophenes such as 4-cyanobenzothiophene and 5-cyanobenzothiophene; halobenzothiophenes such as 4-chlorobenzothiophene, 5-chlorobenzothiophene, 6-chlorobenzothiophene and 4-bromobenzothiophene; halogenated alkyl benzothiophenes such as 4-trifluoromethyl benzothiophene and 5-trifluoromethyl benzothiophene; carbamoyl benzothiophenes such as 4-carbamoyl benzothiophene, 5-dimethylcarbamoyl benzothiophene and 6-dimethylcarbamoyl benzothiophene; acyl benzothiophenes such as 4-acetyl benzothiophene, 5-acetyl benzothiophene and 6-butanoyl benzothiophene; alkoxycarbonyl benzothiophenes such as 4-methoxycarbonyl benzothiophene, 5-methoxycarbonyl benzothiophene and 6-ethoxycarbonyl benzothiophene; N-substituted amino benzothiophenes such as 4-amino benzothiophene, 5-amino benzothiophene, 6-dimethylamino benzothiophene and 4-dimethylamino benzothiophene; alkyl halobenzothiophenes such as 4-chloro-5-butyl benzothiophene and 4-methyl-6-chlorobenzothiphene; alkoxyalkyl benzothiophenes such as 2-methoxy-4-methyl benzothiophene, 2-methoxy-5-methyl benzothiophene and 2-ethoxy-5-methyl benzothiophene; halocyanobenzothiophenes such as 4-chloro-6-cyanobenzothiophene; pyrrole; halopyrroles such as 2-chloropyrrole, 3-chloropyrrole, 4-chloropyrrole and 2-bromopyrrole; alkyl pyrroles such as 3-methyl pyrrole, 4-methyl pyrrole, 5-methyl pyrrole, 3-isopropyl pyrrole, 2-isopropyl pyrrole, 4-isopropyl pyrrole, 5-isopropyl pyrrole, 2-isopropyl pyrrole, 3-isobutyl pyrrole, 3,4-dimethyl pyrrole, 3-butyl-4-methyl pyrrole, 2,5-dimethyl pyrrole, 3,4-diisopropyl pyrrole, 2-isopropyl-3-methyl pyrrole, 3-butyl-4-isopropyl pyrrole and 2-butyl-5-isopropyl pyrrole; alkoxy pyrroles such as 3-methoxy pyrrole, 2-ethoxy pyrrole, 3-butoxy pyrrole, 2-isopropoxy pyrrole, 2-methoxy pyrrole, 3-ethoxy pyrrole and 2-methoxy pyrrole; nitropyrroles such as 2-chloro-3-methoxy pyrrole, 2-chloro-4-methoxy pyrrole, 2-chloro-5-ethoxy pyrrole, 3-nitropyrrole and 2-nitropyrrole; cyanopyrroles such as 3-cyanopyrrole and 2-cyanopyrrole; halogenated pyrroles such as 3-chloropyrrole, 2-chloropyrrole, 3-bromopyrrole and 2-bromopyrrole;

halogenated alkyl pyrroles such as 3-trifluoromethyl pyrrole and 2-trifluoromethyl pyrrole; carbamoyl pyrroles such as 3-carbamoyl pyrrole, 2-dimethylcarbamoyl pyrrole and 4-dimethylcarbamoyl pyrrole; acyl pyrroles such as 3-acetyl pyrrole, 2-acetyl pyrrole and 3-butanoyl pyrrole; alkoxycarbonyl pyrroles such as 3-methoxycarbonyl pyrrole, 2-methoxycarbonyl pyrrole and 3-ethoxycarbonyl pyrrole; N-substituted amino pyrroles such as 2-amino pyrrole, 3-amino pyrrole, 2-dimethylamino pyrrole and 3-dimethylamino pyrrole; alkyl halopyrroles such as 4-chloro-3-butyl pyrrole and 4-methyl-2-chloropyrrole; alkoxyalkyl pyrroles such as 2-methoxy-3-methyl pyrrole, 2-methoxy-4-methyl pyrrole and 2-ethoxy-5-methyl pyrrole; cyano-substituted chloropyrroles such as 3-chloro-2-cyanopyrrole, 3-chloro-4-cyanopyrrole, 3-chloro-5-cyanopyrrole, 4-chloro-2-cyanopyrrole and 4-chloro-3-cyanpyrrole; nitro-substituted chloropyrroles such as 3-chloro-2-nitropyrrole, 3-chloro-4-nitropyrrole, 3-chloro-5-nitropyrrole, 4-chloro-2-nitropyrrole and 4-chloro-3-nitropyrrole; amino chloropyrroles such as 3-chloro-4-amino pyrrole, 3-chloro-5-dimethylamino pyrrole, 4-chloro-2-dimethylamino pyrrole and 4-chloro-3-dimethylamino pyrrole; carbamoyl chloropyrroles such as 3-chloro-4-carbamoyl pyrrole, 3-chloro-5-dimethylcarbamoyl pyrrole, 4-chloro-2-dimethylcarbamoyl pyrrole and 4-chloro-3-dimethylcarbamoyl pyrrole; halogenated alkyl halopyrroles such as 4-chloro-2-trifluoromethyl pyrrole and 4-chloro-3-trifluoromethyl pyrrole; N-substituted pyrroles having, or a nitrogen of the pyrrole ring of the aforementioned pyrroles, a substituent such as an alkyl group such as a methyl, ethyl or benzyl group, acyl group such as an acetyl, benzoyl or butanoyl group, substituted silyl group such as a t-butyldimethylsilyl or trimethylsilyl group, or alkoxycarbonyl group such as a methoxycarbonyl or phenoxycarbonyl group; indole; alkyl indoles such as 6-methyl indole, 4-methyl indole, 5-methyl indole, 4-isopropyl indole, 2-isopropyl indole, 6-isopropyl indole, 3-isobutyl indole, 5,6-dimethyl indole, 4-butyl-6-methyl indole, 2,5-dimethyl indole, 3,4-diisopropyl indole, 4-isopropyl-5-methyl indole, 4-butyl-6-isopropyl indole and 2-butyl-5-isopropyl indole; alkoxy indoles such as 4-methoxy indole, 4-ethoxy indole, 5-butyoxy indole, 6-isopropoxy indole, 5-methoxy indole, 6-ethoxy indole and 2-methoxy indole; nitroindoles such as 4-nitroindole and 5-nitroindole; cyanoindoles such as 4-cyanoindole and 5-cyanoindole; haloindoles such as 4-chloroindole, 5-chloroindole, 6-chloroindole and 4-bromoindole; halogenated alkyl indoles such as 4-trifluoromethyl indole and 5-trifluoromethyl indole; carbamoyl indoles such as 4-carbamoyl indole, 5-dimethylcarbamoyl indole and 6-dimethylcarbamoyl indole; acyl indoles such as 4-acetyl indole, 5-acetyl indole and 6-butanoyl indole; alkoxycarbonyl indoles such as 4-methoxycarbonyl indole, 5-methoxycarbonyl indole and 6-ethoxycarbonyl indole; N-substituted amino indoles such as 4-amino indole, 5-amino indole, 6-dimethylamino indole and 4-dimethylamino indole; alkyl haloindoles such as 4-chloro-5-butyl indole and 4-methyl-6-chloroindole; alkoxyalkyl indoles such as 2-methoxy-4-methyl indole, 2-methoxy-5-methyl indole and 2-ethoxy-5-methyl indole; halocyanoindoles such as 4-chloro-6-cyanoindole; N-substituted indoles having, on a nitrogen on the pyrrole ring of the aforementioned indoles, a substituent such as an alkyl group such as a methyl, ethyl or benzyl group, acyl group such as an acetyl, benzoyl or butanoyl group, substituted silyl group such as a t-butyldimethylsilyl or trimethylsilyl group, or alkoxycarbonyl group such as a methoxycarbonyl or phenoxycarbonyl group; pyridine; alkyl pyridines such as 2-methyl pyridine, 3-methyl pyridine, 2-ethyl pyridine, 3-isopropyl pyridine, 2-isopropyl pyridine, 2-butyl pyridine, 3-butyl pyridine, 2-isobutyl pyridine, 3-isobutyl pyridine, 3,4-dimethyl pyridine, 3-butyl-4-methyl pyridine, 2,5-dimethyl pyridine, 3,4-diisopropyl pyridine, 2-isopropyl-3-methyl pyridine, 3-butyl-4-isopropyl pyridine and 2-butyl-5-isopropyl pyridine; alkoxy pyridines such as 3-methoxy pyridine, 2-ethoxy pyridine, 3-butyoxy pyridine, 2-isopropoxy pyridine, 2-methoxy pyridine and 3-ethoxy pyridine; nitropyridines such as 3-nitropyridine and 2-nitropyridine; cyanopyridines such as 3-cyanopyridine and 2-cyanopyridine; halopyridines such as 2-chloropyridine, 3-chloropyridine, 4-chloropyridine and 2-bromopyridine; halogenated alkyl pyridines such as 3-trifluoromethyl pyridine and 2-trifluoromethyl pyridine; carbamoyl pyridines such as 3-carbamoyl pyridine, 2-dimethylcarbamoyl pyridine and 4-dimethylcarbamoyl pyridine; acyl pyridines such as 3-acetyl pyridine, 2-acetyl pyridine and 3-butanoyl pyridine; alkoxycarbonyl pyridines such as 3-methoxycarbonyl pyridine, 2-methoxycarbonyl pyridine and 3-ethoxycarbonyl pyridine; N-substituted amino pyridines such as 2-amino pyridine, 3-amino pyridine, 2-dimethylamino pyridine and 3-dimethylamino pyridine; alkyl halopyridines such as 4-chloro-3-butyl pyridine and 4-methyl-2-chloropyridine; alkoxyalkyl pyridines such as 2-methoxy-3-methyl pyridine, 2-methoxy-4-methyl pyridine and 2-ethoxy-5-methyl pyridine; cyano-substituted chloropyridines such as 3-chloro-2-cyanopyridine, 3-chloro-4-cyanopyridine, 3-chloro-5-cyanopyridine, 4-chloro-2-cyanopyridine and 4-chloro-3-cyanopyridine; nitro-substituted chloropyridines such as 3-chloro-2-nitropyridine, 3-chloro-4-nitropyridine, 3-chloro-5-nitropyridine, 4-chloro-2-nitropyridine and 4-chloro-3-nitropyridine; amino chloropyridines such as 3-chloro-4-amino pyridine, 3-chloro-5-dimethylamino pyridine, 4-chloro-2-dimethylamino pyridine and 4-chloro-3-dimethylamino pyridine; carbamoyl chloropyridines such as 3-chloro-4-carbamoyl pyridine, 3-chloro-5-dimethylcarbamoyl pyridine, 4-chloro-2-dimethylcarbamoyl pyridine and 4-chloro-3-dimethylcarbamoyl pyridine; halogenated alkyl halopyridines such as 4-chloro-2-trifluoromethyl pyridine, 4-chloro-3-trifluoromethyl pyridine; quinoline; alkyl quinolines such as 6-methyl quinoline, 4-methyl quinoline, 5-methyl quinoline, 4-isopropyl quinoline, 2-isopropyl quinoline, 6-isopropyl quinoline, 3-isobutyl quinoline, 5,6-dimethyl quinoline, 4-butyl-6-methyl quinoline, 2,5-dimethyl quinoline, 3,4-diisopropyl quinoline, 4-isopropyl-5-methyl quinoline, 4-butyl-6-isopropyl quinoline and 2-butyl-5-isopropyl quinoline; alkoxy quinolines such as 4-methoxy quinoline, 4-ethoxy quinoline, 5-butoxy quinoline, 6-isopropoxy quinoline, 5-methoxy quinoline, 6-ethoxy quinoline and 2-methoxy quinoline; nitroquinolines such as 4-nitroquinoline and 5-nitroquinoline; cyanoquinolines such as 4-cyanoquinoline and 5-cyanoquinoline; haloquinolines such as 4-chloroquinoline, 5-chloroquinoline, 6-chloroquinoline and 4-bromoquinoline; halogenated alkyl quinolines such as 4-trifluoromethyl quinoline and 5-trifluoromethyl quinoline; carbamoyl quinolines such as 4-carbamoyl quinoline, 5-dimethylcarbamoyl quinoline and 6-dimethylcarbamoyl quinoline; acyl quinolines such as 4-acetyl quinoline, 5-acetyl quinoline and 6-butanoyl quinoline; alkoxycarbonyl quinolines such as 4-methoxycarbonyl quinoline, 5-methoxycarbonyl quinoline and 6-ethoxycarbonyl quinoline; N-substituted amino quinolines such as 4-amino quinoline, 5-amino quinoline, 6-dimethylamino quinoline and 4-dimethylamino quinoline; alkyl haloquinolines such as 4-chloro-5-butyl quinoline and 4-methyl-6-chloroquinoline; alkoxyalkyl quinolines such as 2-methoxy-4-methyl quinoline, 2-methoxy-5-methyl quinoline and 2-ethoxy-5-methyl quinoline; halocyanoquinolines such as 4-chloro-6-cyanoquinoline; and, imidazoles, triazoles, oxazoles, thiazoles, pyrazoles, isoxazoles, isothiazoles, pyrazines, pyrimidines and pyridazines having substituents such as a hydrogen atom, linear or branched $C_{1-8}$ alkyl group, linear or branched $C_{1-8}$ alkoxy group, nitro group, cyano group, halogenated $C_{1-8}$ alkyl group, halogen atom, carbamoyl group, $C_{1-8}$ acyl group, $C_{1-8}$ alkoxycarbonyl group or substituted or non-substituted amino group.

Although the iridium-containing catalyst used in the present invention may be any such catalyst provided it is a compound that contains iridium (Ir), the iridium-containing catalyst is preferably a catalyst represented by the following general formula (X):

composed of a cation portion represented by Ir, an anion portion represented by A and an alkene portion represented by B. More preferably, the anion portion represented by A is a chlorine atom, alkoxy group, hydroxyl group or phenyloxy group which may or may not have a substituent, B is an alkene-containing compound such as COD (1,5-cyclooctadiene), COE (1-cyclooctene) or indene, and n is 1 or 2. Specific examples include IrCl(COD), IrCl(COE)$_2$, Ir(OMe)(COD), Ir(OH)(COD) and Ir(OPh)(COD). The amount used is 1/100000 to 1 mole, and preferably 1/10000 mole to 1/10 mole, with respect to bis(pinacolate)diboron or pinacol borane.

Although there are no particular restrictions on the ligand in the present invention provided it is a Lewis base having the ability to coordinate to an iridium-containing catalyst, it is preferably a bidentate Lewis base compound, and more preferably, a compound represented with the following general formula (XI) having a partial structure of bipyridine which may or may not have a substituent:

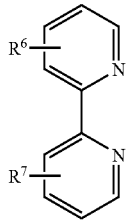

(wherein, $R^6$ and $R^7$ may be the same or different and respectively represent a hydrogen atom, linear or branched $C_{1-8}$ alkyl group, linear or branched $C_{1-8}$ alkoxy group, nitro group, cyano group, halogenated $C_{1-8}$ alkyl group, halogen atom, carbamoyl group, $C_{1-8}$ acyl group, $C_{1-8}$ alkoxycarbonyl group or amino group which may or may not have a substituent, or the following general formula (II) in which $R^6$ and $R^7$ are substituted at position 6 and position 6':

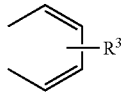

(wherein, $R^3$ represents a hydrogen atom, linear or branched $C_{1-8}$ alkyl group, linear or branched $C_{1-8}$ alkoxy group, nitro group, cyano group, halogenated $C_{1-8}$ alkyl group, halogen atom, carbamoyl group, $C_{1-8}$ acyl group, $C_{1-8}$ alkoxycarbonyl group, or amino group which may or may not have a substituent), specific examples of which include trialkyl phosphines such as triphenyl phosphine and tributyl phosphine; ethylenediamines such as tetramethylethylenediamine and ethylenediamine; bipyridines such as 4,4'-di-t-butyl bipyridine, 2,2'-bipyridine, 4,4'-di-methoxy bipyridine, 4,4'-bis(dimethylamino)bipyridine, 4,4'-dichlorobipyridine and 4,4'-dinitrobipyridine, and 1,10-phenanthroline, and preferable specific examples including bipyridines such as 4,4'-di-t-butyl bipyridine, 2,2'-bipyridine, 4,4'-di-methoxybipyridine, 4,4'-bis(dimethylamino)bipyridine, 4,4'-dichlorobipyridine and 4,4'-dinitrobipyridine. The amount used is 1/100000 mole to 1 mole, and preferably 1/10000 mole to 1/10 mole, with respect to bis(pinacolate)diboron or pinacol borane.

Although the reaction of the present invention can be carried out in the absence of solvent, a solvent can be used as is suitable. There are no particular restrictions on the solvent used in the present invention provided it does not have an effect on the reaction, and examples of such solvents include hydrocarbons such as octane, pentane, heptane and hexane; amides such as dimethylformamide and dimethylacetoamide; pyrrolidones such as N-methyl-2-pyrrolidone; ketones and sulfoxides such as acetone, ethyl methyl ketone and dimethylsulfoxide; aromatic hydrocarbons such as benzene, toluene, xylene and mesitylene; nitrites such as acetonitrile; ethers such as diisopropyl ether, tetrahydrofuran, 1,4-dioxane, 1,2-dimethoxyethane and anisole; and alcohols such as methanol, ethanol, propanol, ethylene glycol and propylene glycol; with hydrocarbons such as octane, pentane, heptane and hexane being preferable. The reaction is carried out within a temperature range of 0 to 180° C. and preferably 10 to 150° C.

Monoboronation and diboronation can be adjusted to a desired formation ratio by suitably selecting the ratios used of the aforementioned aromatic heterocyclic compound (I) or (VII) and the aforementioned boron compound represented by (III) or (IV). The formation ratio of monoboronation and diboronation change according to the ratio of aromatic heterocyclic compound (I) or (VII) to boron compound (III) or (IV), and the greater aromatic heterocyclic compound (I) or (VII) is used in excess, the higher the priority of the occurrence of monoboronation. Normally, in the case of targeting monoboronation, 2-fold to 100-fold moles, and preferably 2-fold to 50-fold moles, of aromatic heterocyclic compound (I) or (VII) are used relative to the boron compound of (III) or (IV). In addition, in the case of targeting diboronation, 1/100-fold moles to 2-fold moles, and preferably 1/10-fold moles to 1.5-fold moles, of aromatic heterocyclic compound (I) or (VII) are used relative to the boron compound of (III) or (IV).

Although varying according to the amount of catalyst, a reaction temperature and so forth, the reaction time is normally 0.2 to 120 hours, and preferably 2 to 24 hours. In addition, the reaction is preferably carried out in an inert gas atmosphere to prevent deactivation of the catalyst caused by oxygen during the reaction. Examples of inert gases include nitrogen gas and argon gas. In addition, although there are no particular restrictions on the reaction pressure, the reaction is normally carried out at atmospheric pressure.

Although target compounds of the present invention in the form of aromatic heterocyclic boron compounds represented by general formulas (V), (VI), (VIII) and (IX) are obtained in this manner, ordinary purification procedures can be carried out to improve purity, examples of which include washing with saturated saltwater, concentration, precipitation, crystallization and distillation. In addition, the resulting target compounds can be treated with silica gel, alumina and so forth.

EXAMPLES

Although the following provides a more detailed explanation of the present invention based on its examples, the present invention is not limited to only these examples.

Example 1

Synthesis of 2-(4,4,5,5-tetramethyl-1,3,2-dioxaborolan-2-yl)thiophene

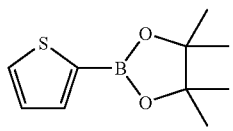

Bis(pinacolate)diboron (1 mmol), aromatic heterocyclic compound in the form of thiophene (10 mmol), catalyst in the form of IrCl(COD) (0.03 mmol), ligand in the form of dtbpy (0.03 mmol) and 6 ml of octane were mixed followed by stirring while heating for 16 hours at 80° C. After allowing to cool to room temperature, the mixture was diluted with toluene and washed with saturated saltwater. The organic layer was concentrated under reduced pressure followed by distilling off the residue to obtain 2-(4,4,5,5-tetramethyl-1,3,2-dioxaborolan-2-yl)thiophene at a yield of 75%.

$^1$H-NMR (400 MHz, CDCl$_3$, TMS): δ 1.35 (s, 12H), 7.20 (dd, 1H, J=3.7 and 4.6 Hz), 7.64 (d, 1H, J=4.6 Hz), 7.66 (d, 1H, J=3.4 Hz)

$^{13}$C-NMR (100 MHz, CDCl$_3$, TMS): δ 24.75, 84.07, 128.21, 132.35, 137.14

MS m/e: 43(33), 110(50), 111(100), 124(82), 195(72), 210 (M$^+$, 96)

Exact mass calculated for C$_{10}$H$_{15}$BO$_2$S: 210.0886. found: 210.0881

Example 2

Synthesis of 2-(4,4,5,5-tetramethyl-1,3,2-dioxaborolan-2-yl)thiophene

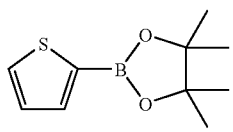

The same procedure as Example 1 was repeated with the exception of using bpy instead of dtbpy for the ligand. The yield was 60%.

Example 3

Synthesis of 2-(4,4,5,5-tetramethyl-1,3,2-dioxaborolan-2-yl)thiophene

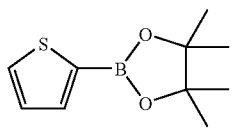

The same procedure as Example 1 was repeated with the exception of using Ir(OMe)(COD) instead of IrCl(COD) for the catalyst, and allowing to react for 4 hours at 25° C. The yield was 88%.

Example 4

Synthesis of 2-(4,4,5,5-tetramethyl-1,3,2-dioxaborolan-2-yl)thiophene

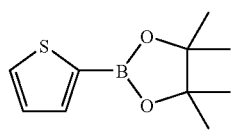

The same procedure as Example 1 was repeated with the exception of using Ir(OH)(COD) instead of IrCl(COD) for the catalyst and allowing to react for 4 hours at 25° C. The yield was 86%.

Example 5

Synthesis of 2-(4,4,5,5-tetramethyl-1,3,2-dioxaborolan-2-yl)thiophene

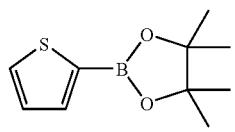

The same procedure as Example 1 was repeated with the exception of using Ir(OPh)(COD) instead of IrCl(COD) for the catalyst and allowing to react for 4 hours at 25° C. The yield was 82%.

Example 6

Synthesis of 2-(4,4,5,5-tetramethyl-1,3,2-dioxaborolan-2-yl)thiophene

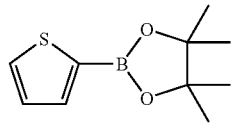

The same procedure as Example 1 was repeated with the exception of using 1.0 mmol of pinacol borane instead of bis(pinacolate)diboron. The yield was 75%.

Example 7

Synthesis of 2-methyl-5-(4,4,5,5-tetramethyl-1,3,2-dioxaborolan-2-yl)thiophene

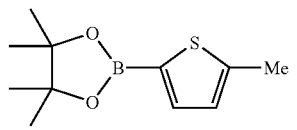

The same procedure as Example 1 was repeated with the exception of using 2-methyl thiophene instead of thiophene for the aromatic heterocyclic compound. The yield was 85%.

¹H-NMR (400 MHz, CDCl₃, TMS): δ 1.33 (s, 12H), 2.53 (s, 3H), 6.84 (d, 1H, J=3.4 Hz), 7.45 (d, 1H, J=3.4 Hz)

¹³C-NMR (100 MHz, CDCl₃, TMS): δ 15.36, 24.72, 83.85, 126.98, 137.62, 147.52

MS m/e: 123(31), 124(76), 138(85), 209(49), 224(M⁺, 100)

Exact mass calculated for $C_{11}H_{17}BO_2S$: 224.1042. found: 224.1044

Example 8

Synthesis of (4,4,5,5-tetramethyl-1,3,2-dioxaborolan-2-yl)furan

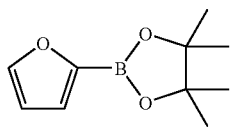

The same procedure as Example 1 was repeated with the exception of using furan instead of thiophene for the aromatic heterocyclic compound. The yield was 80% (2-position boronation/3-position boronation=92/8).

¹H-NMR (400 MHz, CDCl₃, TMS): δ (2-isomer) 1.35 (s, 12H), 6.45 (dd, 1H, J=1.7 and 3.4 Hz), 7.08 (d, 1H, J=3.4 Hz), 7.66 (d, 1H, J=1.4 Hz); δ (3-isomer) 1.32 (s, 12H), 6.59 (dd, 1H, J=0.7 and 1.7 Hz), 7.47 (t, 1H, J=1.5 Hz), 7.78 (m, 1H)

¹³C-NMR (100 MHz, CDCl₃, TMS): δ (2-isomer) 24.73, 84.20, 110.30, 123.19, 141.31; (3-isomer) not observed MS m/e: 43(33), 95(28), 109(31), 151(100), 179(29), 194 (M⁺, 39)

Exact mass calculated for $C_{10}H_{15}BO_3$: 194.1114. found: 194.1122

Example 9

Synthesis of 2-(4,4,5,5-tetramethyl-1,3,2-dioxaborolan-2-yl)pyrrole

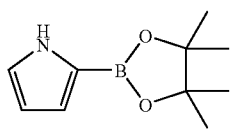

The same procedure as Example 1 was repeated with the exception of using pyrrole instead of thiophene for the aromatic heterocyclic compound. The yield was 60%.

¹H-NMR (400 MHz, CDCl₃, TMS): δ 1.32 (s, 12H), 6.30 (ddd, 1H, J=2.3, 2.3 and 3.4 Hz), 6.85 (ddd, 1H, J=1.2, 2.2 and 3.4 Hz), 7.00 (ddd, 1H, J=1.2, 2.4 and 2.4 Hz), 8.79 (br s, 1H)

¹³C-NMR (100 MHz, CDCl₃, TMS): δ 24.75, 83.56, 109.70, 119.99, 122.64

MS m/e: 107(49), 178(41), 193(M⁺, 100)

Example 10

Synthesis of (4,4,5,5-tetramethyl-1,3,2-dioxaborolan-2-yl)pyridine

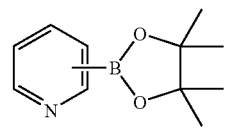

The same procedure as Example 1 was repeated with the exception of using 2 mmol of pyridine instead of thiophene for the aromatic heterocyclic compound. The yield was 60%.

¹H-NMR (400 MHz, CDCl₃, TMS): δ (4-isomer), (3-isomer);

¹³C-NMR (100 MHz, CDCl₃, TMS): δ (4-isomer), (3-isomer);

MS m/e: 105(32), 106(73), 119(100), 190(99), 205(M⁺, 90)

Exact mass calculated for $C_{11}H_{16}BNO_2$: 205.1274. found: 205.1265

Example 11

Synthesis of 2-(4,4,5,5-tetramethyl-1,3,2-dioxaborolan-2-yl)benzo[b]thiophene

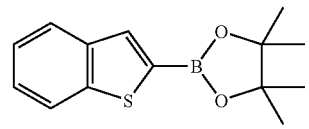

The same procedure as Example 1 was repeated with the exception of using 4 mmol of benzothiophene instead of thiophene for the aromatic heterocyclic compound. The yield was 85%.

¹H-NMR (400 MHz, CDCl₃, TMS): δ 1.38 (s, 12H), 7.35 (ddd, 1H, J=1.7, 7.3 and 8.8 Hz), 7.37 (ddd, 1H, J=1.8, 7.1 and 9.0 Hz), 7.85 (dd, 1H, J=2.2 and 9.0 Hz), 7.89 (s, 1H), 7.91 (dd, 1H, J=1.5 and 9.0 Hz)

¹³C-NMR (100 MHz, CDCl₃, TMS): δ 24.80, 84.43, 122.51, 124.08, 124.36, 125.29, 134.48, 140.43, 143.71

MS m/e: 160(80), 174(87), 259(25), 260(M⁺, 100)

Exact mass calculated for $C_{14}H_{17}BO_2S$: 260.1042. found: 260.1038

Example 12

Synthesis of 2-(4,4,5,5-tetramethyl-1,3,2-dioxaborolan-2-yl)benzo[b]furan

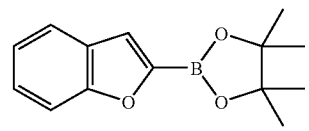

The same procedure as Example 1 was repeated with the exception of using 4 mmol of benzofuran instead of thiophene for the aromatic heterocyclic compound. The yield was 87% (2-position boronation/3-position boronation=93/7).

$^1$H-NMR, (400 MHz, CDCl$_3$, TMS): δ (2-isomer) 1.39 (s, 12H), 7.23 (t, 1H, J=7.4 Hz), 7.34 (dt, 1H, J=1.2 and 7.8 Hz), 7.40 (s, 1H), 7.57 (d, 1H, J=8.5 Hz), 7.63 (d, 1H, J=7.8 Hz), (3-isomer) 1.37 (s, 12H), 7.26 (ddd, 1H, J=1.8, 7.3 and 9.3 Hz), 7.29 (ddd, 1H, J=2.1, 7.3 and 9.5 Hz), 7.50 (dd, 1H, J=2.4 and 6.6 Hz), 7.92 (dd, 1H, J=2.7 and 9.5 Hz), 7.92 (dd, 1H, J=2.7 and 6.3 Hz), 7.95 (s, 1H)

$^{13}$C-NMR (100 MHz, CDCl$_3$, TMS): δ (2-isomer) 24.77, 84.68, 111.97, 119.53, 121.88, 122.71, 125.93, 127.48, 157.51; (3-isomer) not observed MS m/e: 144(38), 158(25), 201(100), 244(M$^+$, 72)

Exact mass calculated for C$_{14}$H$_{17}$BO$_3$: 244.1271. found: 244.1274

Example 13

Synthesis of 2-(4,4,5,5-tetramethyl-1,3,2-dioxaborolan-2-yl)indole

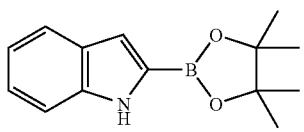

The same procedure as Example 1 was repeated with the exception of using 4 mmol of indole instead of thiophene for the aromatic heterocyclic compound. The yield was 89%.

$^1$H-NMR (400 MHz, CDCl$_3$, TMS): δ 1.36 (s, 12H), 7.09 (t, 1H, J=7.7 Hz), 7.11 (s, 1H), 7.23 (t, 1H, J=8.3 Hz), 7.38 (d, 1H, J=8.3 Hz), 7.67 (d, 1H, J=7.8 Hz), 8.56 (br s, 1H)

$^{13}$C-NMR (100 MHz, CDCl$_3$, TMS): δ 24.81, 84.13, 111.24, 113.84, 119.77, 121.58, 123.61, 128.27, 138.20

MS m/e: 143(35), 186(42), 242(27), 243(M$^+$, 100)

Exact mass calculated for C$_{14}$H$_{18}$BNO$_2$: 243.1431. found: 243.1438

Example 14

Synthesis of 3-(4,4,5,5-tetramethyl-1,3,2-dioxaborolan-2-yl)-1-(triisopropylsilyl)indole

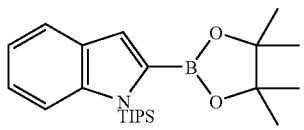

The same procedure as Example 1 was repeated with the exception of using 4 mmol of N-triisopropylsilyl indole instead of thiophene for the aromatic heterocyclic compound. The yield was 81%.

$^1$H-NMR (400 MHz, CDCl$_3$, TMS): δ 1.14 (d, 18H, J=7.6 Hz), 1.37 (s, 12H), 1.74 (qq, 3H, J=7.6 and 7.6 Hz), 7.13 (ddd, 1H, J=1.8, 7.3 and 9.0 Hz), 7.16 (ddd, 1H, J=1.5, 7.1 and 8.5 Hz), 7.50 (dd, 1H, J=2.3 and 6.5 Hz), 7.67 (s, 1H), 8.06 (dd, 1H, J=2.8 and 6.2 Hz)

$^{13}$C-NMR (100 MHz, CDCl$_3$, TMS): δ 12.73, 18.13, 24.96, 82.69, 113.71, 120.41, 121.48, 122.36, 135.13, 141.19, 141.84

MS m/e: 230(28), 356(27), 399(M$^+$, 100)

Exact mass calculated for C$_{23}$H$_{38}$BNO$_2$Si: 399.2764. found: 399.2766

Example 15

Synthesis of 1-methyl-3-(4,4,5,5-tetramethyl-1,3,2-dioxaborolan-2-yl)indole

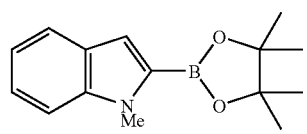

The same procedure as Example 1 was repeated with the exception of using 4 mmol of N-methyl indole instead of thiophene for the aromatic heterocyclic compound. The yield was 64%.

Example 16

Synthesis of 3-(4,4,5,5-tetramethyl-1,3,2-dioxaborolan-2-yl)quinoline

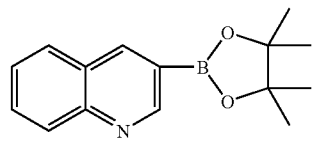

The same procedure as Example 1 was repeated with the exception of using quinoline instead of thiophene for the aromatic heterocyclic compound and reacting at 100° C. The yield was 81%.

$^1$H-NMR (400 MHz, CDCl$_3$, TMS): δ 1.40 (s, 12H), 7.57 (t, 1H, J=7.4 Hz), 7.77 (t, 1H, J=7.7 Hz), 7.86 (d, 1H, J=8.1 Hz), 8.16 (d, 1H, J=8.1 Hz), 8.66 (s, 1H), 9.21 (s, 1H)

$^{13}$C-NMR (100 MHz, CDCl$_3$, TMS): δ 24.93, 84.35, 126.48, 127.58, 128.42, 129.37, 130.54, 144.28, 149.45, 154.81

MS m/e: 155(89), 169(54), 198(37), 240(83), 255(M$^+$, 100)

Exact mass calculated for C$_{15}$H$_{18}$BNO$_2$: 255.1430. found: 255.1427

Example 17

Synthesis of 2,5-bis(4,4,5,5-tetramethyl-1,3,2-dioxaborolan-2-yl)thiophene

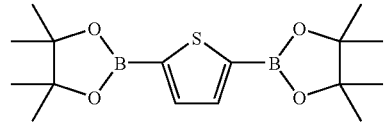

Bis(pinacolate)diboron (1.1 mmol), thiophene (1.0 mmol), IrCl (COD) (0.03 mmol), dtbpy (0.03 mmol) and 6 ml of octane were mixed followed by stirring while heating for 16 hours at 80° C. After allowing to cool to room temperature, the mixture was diluted with toluene and washed with saturated saltwater. The organic layer was concentrated under reduced pressure followed by distilling off the residue to obtain 0.8 mmol of 2,5-bis(4,4,5,5-tetramethyl-1,3,2-dioxaborolan-2-yl)thiophene.

$^1$H-NMR (400 MHz, CDCl$_3$, TMS): δ 1.34 (s, 24H), 7.67 (s, 2H)

$^{13}$C-NMR (100 MHz, CDCl$_3$, TMS): δ 24.74, 84.11, 137.66

MS m/e: 43(50), 59(27), 237(43), 250(100), 321(32), 336 (M$^+$, 55)

Exact mass calculated for C$_{16}$H$_{26}$B$_2$O$_4$S: 336.1738. found: 336.1750

Example 18

Synthesis of bis(4,4,5,5-tetramethyl-1,3,2-dioxaborolan-2-yl)furan

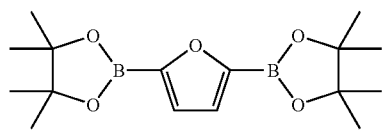

The same procedure as Example 15 was repeated with the exception of using furan instead of thiophene for the aromatic heterocyclic compound. The yield was 70% (2,5-position diboronation/2,4-position diboronation=88/12)

$^1$H-NMR (400 MHz, CDCl$_3$, TMS): δ (2,5-isomer) 1.33 (s, 24H) 7.06 (s, 2H), (2,4-isomer) δ 1.30 (s, 24H), 7.28 (s, 1H), 7.96 (s, 1H)

$^{13}$C-NMR (100 MHz, CDCl$_3$, TMS): δ (2,5-isomer) 24.74, 84.23, 123.30 (2,4-isomer) not observed MS m/e: 83(27), 235(29), 276(47), 277(100), 305(30), 320 (M$^+$, 63)

Exact mass calculated for C$_{16}$H$_{26}$B$_2$O$_5$: 320.1966. found: 320.1962

Example 19

Synthesis of 2,5-bis(4,4,5,5-tetramethyl-1,3,2-dioxaborolan-2-yl)pyrrole

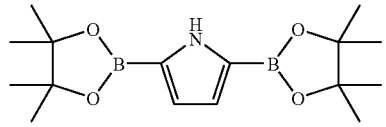

The same procedure as Example 15 was repeated with the exception of using pyrrole instead of thiophene for the aromatic heterocyclic compound. The yield was 79%.

$^1$H-NMR (400 MHz, CDCl$_3$, TMS): δ 1.31 (s, 24H), 6.83 (d, 2H, J=2.0 Hz), 9.28 (br s, 1H)

$^{13}$C-NMR (100 MHz, CDCl$_3$, TMS): δ 24.73, 83.71, 120.35

MS m/e: 234(29), 319(M$^+$, 100)

Exact mass calculated for C$_{16}$H$_{27}$B$_2$NO$_4$: 319.2126. found: 319.2123

Example 20

Synthesis of 2-methoxy-5-(4,4,5,5-tetramethyl-1,3,2-dioxaborolan-2-yl)thiophene

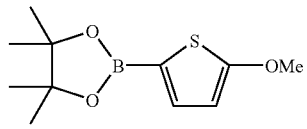

The same procedure as Example 1 was repeated with the exception of using 2-methoxy thiophene instead of thiophene for the aromatic heterocyclic compound. The yield was 82%.

Example 21

Synthesis of 2-(4,4,5,5-tetramethyl-1,3,2-dioxaborolan-2-yl)-5-(trifluoromethyl)thiophene

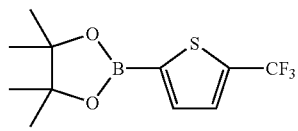

The same procedure as Example 1 was repeated with the exception of using 2-trifluoromethyl thiophene instead of thiophene for the aromatic heterocyclic compound. The yield was 82%.

Example 22

Synthesis of 3-chloro-2-methyl-5-(4,4,5,5-tetramethyl-1,3,2-dioxaborolan-2-yl)thiophene

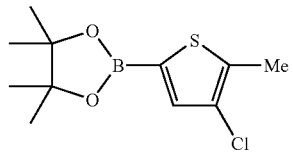

The same procedure as Example 1 was repeated with the exception of using 3-chloro-2-methyl thiophene instead of thiophene for the aromatic heterocyclic compound. The yield was 79%.

Example 23

Synthesis of 3-(4,4,5,5-tetramethyl-1,3,2-dioxaborolan-2-yl)-1-(triisopropylsilyl)pyrrole

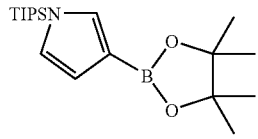

The same procedure as Example 1 was repeated with the exception of using N-triisopropylsilyl pyrrole instead of thiophene for the aromatic heterocyclic compound. The yield was 77%.

$^1$H-NMR (400 MHz, CDCl$_3$, TMS): δ 1.09 (d, 18H, J=7.6 Hz), 1.32 (s, 12H), 1.46 (qq, 3H, J=7.6 and 7.6 Hz), 6.62 (dd, 1H, J=1.2 and 2.4 Hz), 6.81 (br t, 1H, J=2.8 Hz), 7.23 (br d, 1H, J=1.2 Hz)

$^{13}$C-NMR (100 MHz, CDCl$_3$, TMS): δ 11.67, 17.81, 24.87, 82.71, 115.61, 124.96, 133.67

MS m/e: 83(35), 223(51), 224(70), 348(30), 349(M$^+$, 100)

Exact mass calculated for C$_{19}$H$_{36}$BNO$_2$Si: 349.2608. found: 349.2605

INDUSTRIAL APPLICABILITY

According to the production process of the present invention, monoboronation and diboronation can be adjusted to a desired ratio by regulating the ratios used of the aforementioned aromatic heterocyclic compound (I) or (VII) and the aforementioned boron compound represented by (III) or (IV). The present invention is an economical, simple and industrially superior process capable of mono- or diboronating an aromatic heterocyclic compound at high yield, in a single step and under mild conditions.

What is claimed is:

1. A process of producing a heteroaryl boron compound of formula (VIII) or (IX):

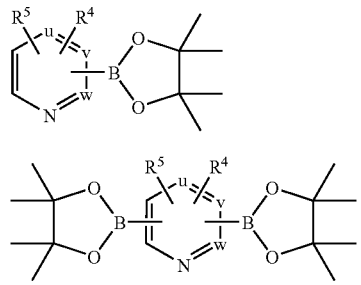

wherein, u, v, w, R$^4$ and R$^5$ are the same as defined below, comprising:

reacting an aromatic heterocyclic compound of formula (VII) with a boron compound of formula (III) or (IV) in the presence of an iridium-containing catalyst of formula (X) and a ligand:

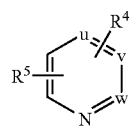

(VII)

wherein u, v and w are each independently —CH= or —N=, and R$^4$ and R$^5$ are each independently a hydrogen atom, a linear or branched C$_{1-8}$ alkyl group, a linear or branched C$_{1-8}$ alkoxy group, a nitro group, a cyano group, a halogenated C$_{1-8}$ alkyl group, a halogen atom, a carbamoyl group, a C$_{1-8}$ acyl group, a C$_{1-8}$ alkoxycarbonyl group, an optionally substituted amino group, or formula (II) in which R$^4$ and R$^5$ are adjacent and form a ring:

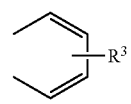

(II)

wherein, R$^3$ is a hydrogen atom, a linear or branched C$_{1-8}$ alkyl group, a linear or branched C$_{1-8}$ alkoxy group, a nitro group, a cyano group, a halogenated C$_{1-8}$ alkyl group, a halogen atom, a carbamoyl group, a C$_{1-8}$ acyl group, a C$_{1-8}$ alkoxycarbonyl group or an optionally substituted amino group:

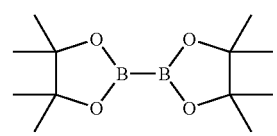

(III)

(IV)

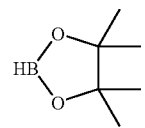

IrABn (X):

wherein, A is an anion portion and B is an alkene portion.

2. The process according to claim 1, wherein
A is a chlorine atom, a linear or branched C$_{1-8}$ alkoxy group, a hydroxyl group or a phenyloxy group which may or may not have a substituent,
B is 1,5-cyclooctadiene or 1-cyclooctene, and
n is 1 or 2.

3. The process according to claim 2, wherein
A is a methoxy group,
B is 1,5-cyclooctadiene and n is 1.

4. The process according to claim 2, wherein A is a chlorine atom, B is 1,5-cyclooctadiene and n is 1.

5. The process according to claim 2, wherein A of is a chlorine atom, B is 1-cyclooctene and n is 2.

6. The process according to claim 1, wherein, the ligand is of formula (XI):

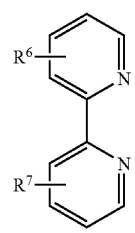

(XI)

wherein

R$^6$ and R$^7$ are each independently, a hydrogen atom, a linear or branched C$_{1-8}$ alkyl group, a linear or branched C$_{1-8}$ alkoxy group, a nitro group, a cyano group, a halogenated C$_{1-8}$ alkyl group, a halogen atom, a carbamoyl group, a C$_{1-8}$ acyl group, a C$_{1-8}$ alkoxycarbonyl group or an amino group which may or may not have a substituent, or of formula (II) wherein R$^6$ and R$^7$ are substituted at positions 3 and 3':

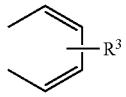 (II)

wherein, $R^3$ is a hydrogen atom, a linear or branched $C_{1-8}$ alkyl group, a linear or branched $C_{1-8}$ alkoxy group, a nitro group, a cyano group, a halogenated $C_{1-8}$ alkyl group, a halogen atom, a carbamoyl group, a $C_{1-8}$ acyl group, a $C_{1-8}$ alkoxycarbonyl group, or an amino group which may or may not have a substituent.

7. The process according to claim 6, wherein the ligand is 2,2'-bipyridine.

8. The process according to claim 6, wherein the ligand is 4,4'-di-tert-butyl-2,2'-bipyridine.

9. The process according to claim 1, wherein the reaction is conducted in the presence of a solvent.

10. The process according to claim 9, wherein the solvent is a hydrocarbon.

11. The process according to claim 1, wherein a reaction temperature is from 0 to 180°.

12. The process according to claim 1, wherein the boron compound is of formula (III) and a molar ratio of the ligand to the boron compound is from 1/100,000 to 1/1.

13. The process according to claim 1, wherein a molar ratio of the compound of formula (VII) to the compound of formula (III) or (IV) is from 2/1 to 100/1.

14. The process according to claim 1, wherein a molar ratio of the compound of formula (VII) to the compound of formula (III) or (IV) is from 1/100 to less than 2/1.

15. The process according to claim 1, wherein the reaction is conducted in an inert gas atmosphere.

* * * * *